United States Patent [19]

Langejan

[11] 4,217,420

[45] * Aug. 12, 1980

[54] ACTIVE DRIED BAKER'S YEAST

[75] Inventor: Arend Langejan, Delft, Netherlands

[73] Assignee: Gist-Brocades N.V., Delft, Netherlands

[*] Notice: The portion of the term of this patent subsequent to Oct. 21, 1991, has been disclaimed.

[21] Appl. No.: 943,134

[22] Filed: Sep. 18, 1978

Related U.S. Application Data

[60] Continuation of Ser. No. 789,423, Apr. 21, 1977, abandoned, which is a continuation of Ser. No. 435,407, Jan. 21, 1974, abandoned, which is a division of Ser. No. 262,727, Jun. 14, 1972, Pat. No. 3,843,800, which is a continuation of Ser. No. 874,723, Nov. 6, 1969, abandoned.

[30] Foreign Application Priority Data

Nov. 8, 1968 [GB] United Kingdom .............. 52950/68

[51] Int. Cl.$^2$ ............................................. C12C 11/32
[52] U.S. Cl. ....................................... 435/256; 426/18; 426/60; 426/62; 426/443; 435/260
[58] Field of Search ............... 195/58, 98, 74; 426/18, 426/19, 60, 62, 443, 518; 435/256, 260, 942

[56] References Cited

U.S. PATENT DOCUMENTS

| | | | |
|---|---|---|---|
| 1,643,047 | 9/1927 | Balls | 426/62 X |
| 2,894,842 | 7/1959 | Mitchell, Jr. et al. | 195/98 X |
| 3,041,249 | 6/1962 | Chen et al. | 195/97 X |
| 3,394,008 | 7/1968 | Lodder et al. | 426/19 |
| 3,780,181 | 12/1973 | Trevelyan | 195/98 X |
| 3,843,800 | 10/1974 | Langejan | 195/98 X |

FOREIGN PATENT DOCUMENTS 1064212 4/1967 United Kingdom .

*Primary Examiner*—David M. Naff
*Attorney, Agent, or Firm*—Hammond & Littell, Weissenberger and Muserlian

[57] ABSTRACT

An active dried bakers' yeast is prepared with a dry matter content of at least 85% by weight, a protein content (%N×6.25) of 45 to 60% based on dry matter and an activity value of 420 to 600, when determined according to test method B$^2$ as defined in the specification. The yeast has the advantages that it can be added as such to the flour prior to dough-making without preliminary soaking, and it is capable of better gas production than active dried yeasts hitherto available.

7 Claims, No Drawings

ACTIVE DRIED BAKER'S YEAST

PRIOR APPLICATIONS

This application is a continuation application of copending application Ser. No. 789,423 filed Apr. 21, 1977, now abandoned, which in turn is a continuation of copending application Ser. No. 435,407 filed Jan. 21, 1974, now abandoned which in turn is a division of my copending, commonly assigned U.S. Pat. application Ser. No. 262,727, now U.S. Pat. No. 3,843,800, filed June 14, 1972 which in turn is a streamlined continuation of application Ser. No. 874,723 filed Nov. 6, 1969, now abandoned.

STATE OF THE ART

Baker's yeast is generally available as compressed yeast with a dry matter content of about 26 to 32% or as active dried yeast with a dry matter content of over 80%, generally more than 90%. Compressed yeast has the disadvantage of relatively poor keeping quality, so that in practice, this kind of yeast is only of interest in countries where the temperature is relatively low and/or fresh yeast is available on a substantially daily basis.

This disadvantage does not apply to active dried yeast which, due to its high dry matter content, is remarkably stable over a prolonged period even at elevated temperatures and is therefore suitable for countries where the temperatures are relatively high, e.g., tropical countries. Active dried yeast, however, has the disadvantage of a relatively low activity and in addition, it has to be subjected to a time-consuming rehydration in water to develop its activity before mixing it with flour for preparing dough.

However, the drawback of a lower activity requiring larger quantities to obtain the same baking results, and consequently higher cost to the baker using commercially available active dried yeast, must be accepted in tropical countries in order to obtain the advantage of the better keeping quality. Consequently in non-tropical countries there is substantially no interest in active dried yeast because of the above-mentioned drawbacks.

The low activity of commercially available active dried yeasts in comparison with that of compressed yeast is shown in the following table. The gas production tests mentioned in this table are described in the examples. The active dried yeasts are from several commercial sources and are indicated by symbols 1 to 5.

active dried yeast as compared with 450 mg (based on dry matter) of compressed yeast. When carrying out gas production tests using equal amounts of yeast, based on dry matter, the gas production values of active dried yeast are considerably lower than that for compressed yeast.

Commercially available active dried yeast generally has a low protein content in the order of 40 to 45% (%N×6.25, N determined by the Kjeldahl method). Such yeasts are fairly stable and resistant to the usual slow drying processes. Experience has shown that yeasts having a high protein content are not suitable for preparing active dry yeast due to the fact that large losses of activity occur during the usually slow drying processes and moreover the product obtained is very unstable. Quick-drying processes, e.g. spray drying, can be applied to yeasts, but such methods also have the disadvantage that they lead to an appreciable loss of activity in the yeast. In addition, very finely divided dusty powders are obtained which give rise to difficulties when they are mixed with flour or when they are re-hydrated.

OBJECTS OF THE INVENTION

It is an object of the invention to provide an active dried baker's yeast having a superior activity.

It is another object of the invention to provide a novel process for the preparation of an active dried baker's yeast.

These and other objects and advantages of the invention will become obvious from the following detailed description.

THE INVENTION

The active dried bakers' yeast of the invention has a dry matter content of at least 85% by weight, a protein content (% N×6.25, as determined by the Kjeldahl method) of 45 to 60% based on dry matter and an activity value of 420 to 600 when determined according to a test method which consists of mixing 480 mg of the dried yeast product in a mixer with 100 g of flour, adding 55 ml of a solution containing 2 g of NaCl and mixing the mass for 6 minutes at 28° C. to form a dough, placing the dough in a water bath maintained at 28° C. and determining the amount of gas produced in the period from 10 to 175 minutes after the start of mixing, expressed in ml at 28° C. and 760 mm Hg (this test procedure is referred to hereafter as test $B^2$.) The yeast

| Samples of Yeast | Form | Dry Matter Content | Protein Content (%N×6.25) on Dry Matter Basis | Phosphorus Content (%$P_2O_5$) on Dry Matter Basis | Test | Gas Production (ml) |
| --- | --- | --- | --- | --- | --- | --- |
| 1 | granules | 92.7 | 42.4 | 1.90 | $A_1$ | 500 |
|   |          |      |      |      | B     | 295 |
| 2 | granules | 92.6 | 41.9 | 1.97 | $A_1$ | 493 |
|   |          |      |      |      | B     | 269 |
| 3 | granules | 92.4 | 41.5 | 1.92 | A     | 444 |
| 4 | particles | 91.6 | 42.7 | 1.36 | A     | 417 |
| 5 | powder | 91.8 | 41.6 | 3.36 | A     | 369 |
| 6 | compressed | 29.0 | 52.5 | 3.20 | $B^3$ | 595 |

This table shows that the gas production values for the commercial active dried yeasts are only comparable to the gas production of compressed yeast of high protein content (Sample 6) when considerably larger amounts of active dried yeast are used, i.e. 930 mg of of the invention has a much higher activity than the active dried yeasts available hitherto and does not require rehydration in order to develop its activity. The yeast of the invention preferably has a dry matter content of from 90 to 96% by weight, a protein content (%N×6.25) of from 48 to 54%, and an activity value of from 480 to 580 when determined according to test $B^2$. The keeping quality of the active dried yeast is comparable to that of the active dried yeasts which are currently commercially available.

For bread-making, the yeast of the invention can be mixed as such with the flour and can readily be homogeneously distributed throughout the dough. A very advantageous property of the yeasts of the invention occurs when they are mixed with the flour and water to form the dough. The yeast particles disintegrate extensively and the yeast becomes homogeneously distributed throughout the dough. This is a property which most active dried yeasts do not possess.

In order to obtain the highest activities, the yeast of the invention preferably contains a swelling agent and/or a wetting agent. Suitable swelling agents, which are preferably used in amounts of from 0.5 to 5%, advantageously 1 to 2%, based on dry matter, are methyl cellulose and carboxymethyl cellulose. Suitable wetting agents, which are preferably used in amounts of from 0.5 to 5%, advantageously 1 to 2%, based on dry matter, are esters of saturated fatty acids, such as fatty acid esters of sorbitan, e.g. sorbitan monolaurate, monoplamitate, monostearate or mono-oleate; fatty acid esters of glycerol, e.g. glyceryl monostearate, a distearate or monopalmitate; fatty acid esters of propylene glycol, e.g. propylene glycol monostearate; or mixtures of two or more of the above mentioned compounds.

The novel process of the invention for preparing an active dried bakers' yeast comprises dividing fresh compressed yeast having a protein content (%N×6.25) of 45 to 60% based on dry matter into particles, and drying these particles in not more than 120 minutes to a dry matter content of at least 85% by weight by a drying gas flow (for example, using fluidized bed techniques) so that the particles are held within a temperature range of from 20° to 50° C. during the drying process to obtain an active dried yeast having an activity value of 420 to 600 when determined according to test method $B^2$. Drying of the yeast particles is preferably carried out at a temperature of from 30° to 35° C.

Preferably the drying time is less than 50 minutes and advantageously less than 20 minutes. In order to keep the particles within the above mentioned temperature range, it is advantageous that the temperature of the drying gas flow at the end of the drying period be lower than at the beginning thereof. At the start of the drying period, the temperature of the drying gas flow can be up to 160° C.

In order to facilitate the drying process and to obtain a final yeast which is easily distributable through the dough, the compressed yeast is divided into small particles, for example by extruding the yeast to form strands and breaking up the strands to form particles, the particles preferably having a cross-section in the range of 0.2 to 2 mm. From yeast particles of this size, a dried yeast end product is obtained consisting of particles having a cross-section within the range of about 0.1 to 1 mm. The process according to the invention may be carried out discontinuously, but is especially suited to being carried out continuously.

The yeast used should be a strain having a good drying stability, for instance strain 1777 described in British Pat. No. 989,247. The compressed yeast which is used as the starting material may be prepared, for example, by a process in which yeast is partially dehydrated by means of a hypotonic solution, e.g. a salt solution, and washed quickly as described in British Pat. No. 763,926. The active dried yeast of the invention may be packed in any of the usual containers, such as tins or plastic bags, in which the dried yeast is preferably kept under a greatly reduced pressure or in a nitrogen atmosphere. Suitable plastic materials are, for example, polyesters, polyamides, polyethylene, laminates of these materials or laminates with for example, aluminum. Another suitable material is regenerated cellulose, provided with a lacquer layer.

In the following examples there are described several preferred embodiments to illustrate the invention. However, it should be understood that the invention is not intended to be limited to the specific embodiments.

The test methods used in the Examples are described herein.

TEST A (for conventional active dried yeast)

930 mg of the active dried yeast is soaked for 10 minutes in 8 ml of water at 35° C. The yeast suspension obtained is mixed with 100 mg of flour and 47 ml of an aqueous solution containing 2 g of NaCl, the temperatures of flour and salt solution being 28° C. The mixture obtained is mixed for 6 minutes into a dough, which is placed in a water bath adjusted to 28° C. The amount of gas produced within the period of from 10 to 175 minutes after the start of mixing is determined in ml at 28° C. and 760 mm Hg.

TEST $B^1$

This test is carried out in the same way as Test A, except that 480 mg of active dried yeast is used instead of 930 mg.

TEST $B^2$ 480 mg of active dried yeast is mixed as such with 100 g of flour in a mixer. After addition of 55 ml of an aqueous solution containing 2 g of NaCl, the mass is mixed for 6 minutes at 28° C. The remaining operations are the same as those in Test A.

TEST $B^3$ (for compressed yeast)

An amount of compressed yeast corresponding to 450 mg of dry matter is suspended in 55 ml of a solution containing 2 g of NaCl. After adding 100 g of flour, the dough is prepared by mixing for 6 minutes at 28° C. The remaining operations are the same as those in Test A.

EXAMPLE 1

A centrifuged and washed yeast suspension of strain Ng. 1777 having a dry matter content of 170 g/l was mixed with a suspension of sorbitan monostearate (wetting agent) in water to give 1 g of sorbitan monostearate per 100 g of dry yeast and the suspension was filtered to give a compressed yeast with a dry matter content of about 30%, a protein content (%N×6.25) of 52.5% based on dry matter, and a wetting agent content of 1% based on dry matter. The compressed yeast was extruded through a perforated plate having orifices of 0.6 mm diameter. The product obtained was dried to 92 to 95% dry matter with a stream of dry air passing through the mass of yeast. The temperature of this air varied during the drying operation; it was 60° C. during the first 6 minutes and was lowered to 40° C. during the next 6 minutes so that the temperature of the yeast was maintained below 40° C. The overall drying time was 12 minutes. The product thus obtained had a fine granular texture and consisted of particles having a length of about 2 mm and a cross-section of about 0.4 mm. The analysis of the product was: dry matter content, 93.4%; protein content (%N×6.25), 54.0% based on dry matter; phosphorus content expressed as $P_2O_5$ based on dry matter, 3.20%. This product could be added, as such without preliminary soaking, to flour in order to prepare a dough and could be completely dispersed in the dough. Gas production according to test $B^2$ was 516 ml.

EXAMPLE 2

By way of comparison, gas production tests were made on (a) a yeast of low protein content and on (b) a yeast of high protein content. Both yeasts were tested (I) before drying, (II) after conventional drum drying lasting about 18 hours and (III) after the fast drying technique of the present invention. The results are set forth in Table II.

| % Dry matter | Protein content (%N × 6.25) based on dry matter | Phosphorus content % $P_2O_5$ based on dry matter | Determination | Gas Production (ml) |
|---|---|---|---|---|
| 93.0 | 49.2 | 3.02 | $B^2$ | 545 |
| 93.4 | 51.3 | 3.13 | $B^2$ | 564 |
| 93.2 | 53.2 | 3.18 | $B^2$ | 556 |

EXAMPLE 5

The method of Example 1 was repeated, except that drying was carried out so that the temperature of the yeast during drying was always about 30° C. For this purpose, air at about 100° C. was first blown through the yeast mass and the air temperature was gradually

| Drying Method | Form | % Dry Content | Protein content (% N×6.25) on dry matter | Phosphorus Content (%$P_2O_5$) on dry matter | Determination Test | Gas Production | Yeast |
|---|---|---|---|---|---|---|---|
| None | Compressed | 30.0 | 41.5 | 1.76 | $B^3$ | 423 | (a)(I) |
| Conventional slow drying | Granules | 92.8 | 42.7 | 1.82 | $B^2$ | (1) | (a)(II) |
| Quick drying of invention | Particles | 93.0 | 41.6 | 1.78 | $B^2$ | 398 | (a)(III) |
| None | compressed | 29.0 | 52.5 | 3.20 | $B^3$ | 595 | (b)(I) |
| Conventional slow drying | granules | 92.7 | 53.2 | 3.24 | $B^2$ | (1) | (b)(II) |
| Quick drying of invention | Particles | 93.4 | 52.6 | 3.20 | $B^2$ | 516 | (b)(III) |

(1) Gas production was not measured, since the granules did not disintegrate homogeneously through the dough.
From the above results it can be seen that yeast (a)(III) had a lower activity than yeast (b)(III).

Also, undried yeast (a)(I) had a lower activity than dried yeast (b)(III), i.e. the undried compressed low protein yeast (a)(I) had a lower activity than the dried yeast (b) (III). Yeasts (a)(II) and (b)(II) were dried by the conventional process and consequently, the particles did not disintegrate and therefore had a very low activity. Accordingly, it can be seen that in order to produce a dried yeast of the invention of high activity, it is necessary to use a hgih protein content compressed yeast starting material and to dry the yeast quickly.

EXAMPLE 3

A yeast suspension having the following properties: dry matter content, 185 g/l; protein content (%N×6.25) based on dry matter, 54.4%; phosphorus content expressed as $P_2O_5$ based on dry matter, 3.25%, was propagated under such conditions that a maximum activity in the fresh condition was obtained. This yeast was processed in the same way as in Example 1 using the same amount of the wetting agent. The product obtained had the following properties, dry matter content, 93.0%; protein content (%N×6.25) based on dry matter, 54.5%; phosphorus content expressed as $P_2O_5$, based on dry matter, 3.26%; gas production according to test $B^2$, 560 ml.

EXAMPLE 4

Three yeast suspensions obtained by propagating the yeast under conditions which gave maximum activity in the fresh condition were dried in the same manner as in Example 1 using the same amount of the wetting agent to give active dried yeasts having the following characteristics:

lowered during drying. The overall drying time was 10 minutes. The analysis of the end product was: dry matter content, 92.4%; protein content (%N×6.25) based on dry matter, 55.4%; phosphorus content expressed as $P_2O_5$, based on dry matter, 3.20%; gas production according to test $B^2$, 528 ml.

EXAMPLE 6

The method of Example 1 was repeated except that during drying air at about 160° C. was first blown through the yeast mass and the air temperature was gradually reduced during drying, care being taken that the temperature of the yeast was maintained below 40° C. The overall drying time was 8 minutes. The analysis of the end product was: dry matter content, 93.3%, protein content (%N×6.25) based on dry matter, 52.4%; phosphorus content expressed as $P_2O_5$ based on dry matter, 3.15%; gas production according to test $B^2$, 520 ml.

EXAMPLE 7

The process of Example 4 was repeated except that the wetting agent was a blend of glyceryl monostearate and glyceryl distearate. The analysis of the end product was: dry matter content (%N×6.25) base on dry matter, 53.2%; phosphorus content expressed on $P_2O_5$ based on dry matter, 3.16%; gas production according to test $B^2$, 521. ml.

EXAMPLE 8

The process of Example 1 was repeated except that 1.5% by weight of sorbitan monolaurate was used instead of 1% by weight of sorbitan monostearate, both based on dry matter.

The results of Table III were obtained by using yeasts cultivated in such a way that varying protein contents were obtained:

TABLE III

| % Dry Matter | Protein Content (%N × 6.25) Based on Dry Matter | Phosphorus Content (% P$_2$O$_5$) Based on Dry Matter | Gas Production Test B$^2$ |
|---|---|---|---|
| 92.4 | 45.9 | 2.81 | 452 |
| 93.5 | 47.4 | 2.85 | 473 |
| 93.5 | 49.8 | 3.05 | 492 |
| 93.5 | 51.3 | 3.12 | 516 |
| 92.7 | 53.4 | 3.13 | 514 |
| 92.5 | 55.6 | 3.20 | 500 |
| 93.5 | 56.7 | 3.19 | 489 |
| 93.0 | 58.5 | 3.20 | 481 |

EXAMPLE 9

The process of Example 1 was repeated except that the sorbitan monostearate was replaced by 1% by weight of methyl cellulose which was added to the compressed yeast before drying. The results obtained are given in the following table.

| % Dry Matter | Protein Content (%N × 6.25) Based on Dry Matter | Phosphorus Content (% P$_2$O$_5$) Based on Dry Matter | Gas Production Test B$^2$ |
|---|---|---|---|
| 93.6 | 51.6 | 3.06 | 493 |
| 93.0 | 52.6 | 3.09 | 500 |

EXAMPLE 10

In order to illustrate the baking quality of the yeast of the invention, comparative baking test were carried out with a preferred form of the product. For these tests, the following yeasts were used: a commercially available compressed yeast with a protein content (%N×6.25) of 46.1%; a dry matter content of 30%, and an activity of 408 (test B$^3$) (Sample A); a commercially available compressed yeast with a protein content (%N×6.25) of 52.5%; a dry matter content of 29.0%; and an activity of 595 (test B$^3$) (Sample B); and the quickly dried active yeast of the invention of strain having a high protein content (%N×6.25) of 52.6%; a dry matter content of 93.4% and an activity of 516 (test B$^2$) (Sample C).

For these tests, 100 parts of flour, 53 parts of water, 2 parts of NaCl and yeast were mixed together. The active dried yeast was mixed with the other components without previous soaking. 1.8 parts of the compressed yeast were used. A quantity of the active dried yeast (Sample C) was used equal to the amount of dry matter present in the compressed yeast. The mixtures thus obtained were mixed for 15 minutes, care being taken to ensure that the temperature of the dough was 26° C. The fermentation times were as follows:

| 1st proof | 30 min. |
|---|---|
| 2nd proof | 25 min. |
| intermediate proof | 30 min. |
| final proof | 60 min. |
| | 145 min. |

The proofing temperature was 28° C. to 30° C. The dough weight for each loaf amounted to 890 g. After 30 minutes baking at a temperature of 250° C., the following loaf volumes were measured.

| Loaf prepared with Sample A | 2925 ml |
|---|---|
| Loaf prepared with Sample B | 3540 ml |
| Loaf prepared with Sample C | 3495 ml |

From these data, it may be seen that the active high protein dried yeast product (Sample C) has a baking quality comparable to that of the compressed yeast from which it was prepared and far superior to fresh yeast of low protein content.

Various modifications of the compositions and process of the invention may be made without departing from the spirit or scope thereof and it is to be understood that the invention is to be limited only as defined in the appended claims.

I claim:

1. An active dried bakers' yeast with a particle size of 0.1 to 1.0 mm with a dry matter content of at least 85% by weight, a protein content (%N×6.25) 45 to 60% based on dry matter and an activity value of 420 to 600 when determined by test method B$^2$ prepared by the steps of dividing a fresh compressed yeast having a protein content (%N×6.25) of 45 to 60% on dry weight basis into a mass of particles having a particle size of 0.2 to 2.0 mm and drying the mass of particles by passing therethrough a drying gas at a temperature of not more than 160° C. in not more than 120 minutes to a dry matter content of at least 85% by weight with a drying gas flow so that the particles are held within a temperature range of from 20° to 50° C. to obtain a dried bakers' yeast, said compressed yeast prior to drying having added thereto at least one member selected from the group consisting of 0.5 l to 5% based on dry matter of the yeast a swelling agent selected from the group consisting of methyl cellulose and carboxymethyl cellulose, and 0.5 to 5% based on dry matter of the yeast a wetting agent selected from the group consisting of an ester of a saturated and unsaturated fatty acid, a fatty acid ester of glycerol, a fatty acid ester of propylene glycol and a mixture of two or more thereof.

2. An active dried bakers' yeast of claim 1 wherein the amount of swelling agent used is 1.0 to 2% based on dry matter.

3. An active dried bakers' yeast of claim 1 wherein the wetting agent is selected from the group consisting of sorbitan monolaurate, sorbitan monopalmitate, sorbitan monostearate, sorbitan mono-oleate, glyceryl monostearate, glyceryl distearate, glyceryl monopalmitate and propylene glycol monostearate.

4. An active dried bakers' yeast of claim 1 wherein the amount of wetting agent used is 1 to 2% based on dry matter.

5. An active dried bakers' yeast of claim 1 having a protein content (%N×6.25) of 48 to 54% on a dry matter basis.

6. An active dried bakers' yeast of claim 1 having an activity value of 480 to 580 when determined according to test method B$^2$.

7. An active dried bakers' yeast of claim 1 having a dry matter content of 90 to 95% by weight.

* * * * *

UNITED STATES PATENT AND TRADEMARK OFFICE
CERTIFICATE OF CORRECTION

PATENT NO. : 4,217,420  Page 1 of 2
DATED : Aug. 12, 1980
INVENTOR(S) : Arend Langejan It is certified that error appears in the above—identified patent and that said Letters Patent is hereby corrected as shown below:

| Col. | Line | |
|---|---|---|
| [57] | Abstract | "(%N X 6.25)" should be --(% N x 6.25)-- |
| 1 | 18 | "Baker's" should be --Bakers'-- |
| 1 | 4 Col. | "(%N X 6.25)" should be --(% N x 6.25)-- |
| 2 | 9 | " " " " " " " " " " " " " " " " " " " |
| 2 | 37 | " " " " " " " " " " " " " " " " " " " |
| 3 | 1 | " " " " " " " " " " " " " " " " " " " |
| 3 | 25 | "plamitate" should be --palmitate-- |
| 3 | 32 | "(%N X 6.25)" should be --(% N x 6.25)-- |
| 4 | 57 | " " " " " " " " " " " " " " " " " " " |
| 5 | 3 | " " " " " " " " " " " " " " " " " " " |
| 5 | 4 Col | " " " " " " " " " " " " " " " " " " " |
| 5 | 44 | "hgih" should be --high-- |
| 5 | 50 | "(%N X 6.25)" should be --(% N x 6.25)-- |
| 5 | 57 | " " " " " " " " " " " " " " " " " " " |
| 6 | 2 Col. | " " " " " " " " " " " " " " " " " " " |
| 6 | 39 | " " " " " " " " " " " " " " " " " " " |
| 6 | 52 | " " " " " " " " " " " " " " " " " " " |
| 6 | 61 | " " " " " " " " " " " " " " " " " " " |
| 7 | 2Col. Table III | " " " " " " " " " " " " " " " " " " " |
| 7 | 2 Col. | " " " " " " " " " " " " " " " " " " " |
| 7 | 44 | " " " " " " " " " " " " " " " " " " " |

UNITED STATES PATENT AND TRADEMARK OFFICE
CERTIFICATE OF CORRECTION

PATENT NO. : 4,217,420  Page 2 of 2
DATED : Aug. 12, 1980
INVENTOR(S) : Arend Langejan It is certified that error appears in the above—identified patent and that said Letters Patent is hereby corrected as shown below:

| Col. | Line | | |
|---|---|---|---|
| 7 | 47 | "(% N X 6.25)" should be | --(% N x 6.25)-- |
| 7 | 50 | " " " " " " | " " " " " " " " " |
| 8 | Claim 1 | " " " " " " | " " " " " " " " " |
| 8 | 41 | "0.51 to 5%" should be | --0.5 to 5%-- |
| 8 | Claim 5 | "(% N X 6.25)" should be | --(% N x 6.25)-- |

Signed and Sealed this

Tenth Day of March 1981

[SEAL]

Attest:

RENE D. TEGTMEYER

Attesting Officer   Acting Commissioner of Patents and Trademarks